United States Patent [19]

Nash

[11] 4,269,785

[45] May 26, 1981

[54] TRIALKYLDITHIOCARBAMATES AND METHOD OF MAKING SAME

[76] Inventor: Lawrence H. Nash, P.O. Box 23837, Ft. Lauderdale, Fla. 33307

[21] Appl. No.: 58,663

[22] Filed: Jul. 18, 1979

Related U.S. Application Data

[63] Continuation of Ser. No. 888,633, Mar. 21, 1978, abandoned, and a continuation-in-part of Ser. No. 717,137, Aug. 24, 1976, abandoned, which is a continuation-in-part of Ser. No. 671,932, Mar. 30, 1976, abandoned.

[51] Int. Cl.³ .................... A01N 47/10; C07C 155/08
[52] U.S. Cl. ................................. 260/455 A; 424/300
[58] Field of Search ................... 260/455 A; 424/300

[56] References Cited

U.S. PATENT DOCUMENTS

| 2,127,375 | 8/1938 | Bousquet | 260/455 A |
| 2,579,384 | 12/1951 | Handy, et al. | 260/455 A |

OTHER PUBLICATIONS

Reid, Organic Chem. of Bivalent Sulfur, Chemical Publishing, Co., Inc., New York, p. 220.
Chem. Abs., 1967, p. 10,702, 115324p.
Journal of Organic Chemistry, Grunwell, J., vol. 35, No. 5, May 1970, pp. 1500–1501, Chem. Abs., 1970, vol. 73, p. 255, 102423q.
Chem. Abs., vol. 71, 1969, 75815w.

*Primary Examiner*—Henry R. Jiles
*Assistant Examiner*—Robert C. Whittenbaugh
*Attorney, Agent, or Firm*—Lowe, King, Price & Becker

[57] ABSTRACT

Disclosed herein are improved, water-soluble compounds of the formula:

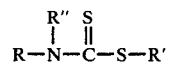

wherein R and R' are each alkyl groups containing from 1 to 6 carbon atoms and R" is hydrogen or an alkyl group of 1 to 6 carbon atoms, said compounds forming clear solutions with no side reaction products present. A process for the preparation of the above compounds comprises reacting 2 moles of at least a mono- or dialkylamine with one mole $CS_2$, in water, and within a reaction chamber which is preferably closed, for a period of time sufficient to cause the pressure therein to fall below normal atmospheric pressure.

4 Claims, No Drawings

TRIALKYLDITHIOCARBAMATES AND METHOD OF MAKING SAME

CROSS-REFERENCE TO RELATED APPLICATIONS

This is a continuation of application Ser. No. 888,633, filed March 21, 1978, now abandoned. Ser. No. 888,633 is a continuation-in-part of my copending U.S. application Ser. No. 717,137, filed Aug. 24, 1976, now abandoned, said application being a continuation-in-part of my U.S. application, Ser. No. 671,932, filed Mar. 30, 1976, now abandoned.

BACKGROUND OF THE INVENTION

This invention relates to novel improved dithiocarbamates that are free of alkali, metal and alkylene thiourea as well as dithiocarbamates that do not form undesired degradation products such as ethylenethiourea (2-imidazolidinethione or ETU). More particularly, this invention relates to di- and trialkyldithiocarbonates that are useful for providing an effective fungicide, insecticide, microbicide and bactericide.

In the past dithiocarbamate compounds, particularly the alkyl esters of dithiocarbamic acid have generally been produced by the reaction of equimolar amounts of mono- or dialkylamine, carbon disulfide and NaOH in the presence of water. The resulting water-soluble products, generally form amber colored liquids, as noted in British Patent Specification No. 805,500, said coloring rendering these materials undesired for application to fruits, vegetables and other agricultural products intended for human consumption because of the discoloring and/or spotting of said products. Thus, the marketability of these products are significantly reduced. In addition, the use of alkali metal hydroxides in the preparation of dithiocarbamates appears to result in the formation of undesired side reaction products, and it is believed that the presence of these side reaction products, which cannot be separated from the dithiocarbamic esters, is believed to be responsible for both the discoloring as well as the environmental hazards associated with dithiocarbamates in the past.

The use of NaOH or KOH in the general reaction results in the formation of the alkali salt which has the general formula: RR'NCSSM wherein M is Na or K. The latter compound is reacted with an alkyl halide which results in the formation of the corresponding alkyl ester of a mono- or dialkyldithiocarbamic acid, said reaction being represented by the following formula:

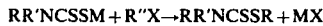

The two reaction products are both quite difficult to separate from one another due to the tendency of the dithiocarbamate ester to decompose when subjected to temperatures above about 80° C. In this regard, it is noted that the boiling points of the dithiocarbamate esters is on the order of about 200° C. with the sodium halides and potassium halides having melting points considerably higher than 200° C. (except for KF which has a melting point of 41° C.).

OBJECTS OF THE INVENTION

It is therefore a primary object of the present invention to provide an improved, effective fungicide, insecticide, microbicide and bactericide that is water soluble and that is particularly effective for the control and removal of undesired pathogens and insects from a given environ, at a reasonable cost.

Consistent with this primary object of this invention, it is also a significant object of this invention to provide an improved dithiocarbamate that is free of alkali, metal and alkylene thiourea, e.g., ETU, and is capable of forming water clear solutions when admixed with water.

Another object of the present invention is the production of novel, improved dithiocarbamates without the employment of alkali metal hydroxides that result in the production of side reaction products and impurities with the desired reaction product.

A further object of this invention is the provision of new improved compounds that exhibit a favorable rate of disappearance from soil after application thereby avoiding residual action by remaining in the soil after the peak desired period for chemical control has passed.

A still further object of the present invention is the provision of new improved compounds that are non-toxic to aquatic life and small animals, and many sulfur sensitive plants.

BRIEF SUMMARY OF THE INVENTION

Compounds of the formula:

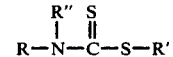

wherein R and R' are each alkyl groups containing from 1 to 6 carbon atoms and R" is hydrogen or an alkyl group of 1 to 6 carbon atoms forming waterclear solutions with no side reaction products present.

A process for preparing the aforementioned compounds comprises reacting 2 moles of at least a mono- or dialkylamine with 1 mole $CS_2$, in water, within preferably, an enclosed reaction chamber for a period of time sufficient for the pressure within said chamber to fall below normal atmospheric pressure, thus resulting in the formation of a dithiocarbamate ester that forms water-clear solutions with no side reaction products, e.g., alkali metal halides, present.

DETAILED DESCRIPTION OF THE INVENTION

As noted herinbefore, each of the alkyl groups present in the novel, improved di- and trialkyldithiocarbamates contains from 1 to 6 carbon atoms and preferably from 1 to 2 carbon atoms. Those compounds containing from 1 to 2 carbon atoms in the alkyl radicals are more soluble in water than those compounds having alkyl groups containing 3 or more carbon atoms.

Best results are achieved with compounds containing 1 or 2 carbon atoms in the alkyl groups because these compounds are capable of removing themselves from the soil and water areas by means of absorption or adsorption.

Pathological pathogens controlled by compounds of this invention include, e.g., diplodia, fusarium colletothricium, phytophthora, rhizoctonia and downy mildew.

When preparing the improved dialkyldithiocarbamates of this invention, two moles of at least one monoalkylamine, containing from 1 to 6 carbon atoms in the alkyl chain, is added to water. The amount of water used is not critical but should be about 300 to 400 grams per mole of amine. To this aqueous solution, 1 mole of CS₂ is added. The ingredients are preferably agitated in a closed reactor for about 5 hours until the pressure is less than atmospheric. The exact time period is not critical to the successful practice of this invention, but the time period for the reaction must be sufficient to insure the drop in atmospheric pressure within the chamber. Once the pressure has dropped to below atmospheric pressure, the reactor is opened and the reaction products are heated to about 50° C., to remove ammonia formed during the reaction. The resulting product, when admixed with water, forms a clear solution with water. No side reaction products are present.

Trialkyldithiocarbamates are preferably prepared by placing 1 mole of dialkylamine, 1 mole of monoalkylamine and 1 mole of CS₂ in water, with said reaction mixture being added to a closed reaction chamber. The reaction mixture is stirred for five hours resulting in a pressure drop below atmospheric pressure. Since the time period for the reaction is somewhat variable and unpredictable, from reaction to reaction, it is important to note that the reaction can be regarded as being complete once the pressure within the chamber is observed to have fallen below atmospheric pressure. Trialkyldithiocarbamate is formed with 1 mole of ammonia. The reaction chamber is opened and the temperature raised to 50° C. resulting in the dissipation of ammonia produced. Each of the alkyl groups in the reactants contain from 1 to 6 carbon atoms thereby resulting in the formation of a product containing from 1 to 6 carbon atoms in each alkyl group.

In producing the di- and trialkyldithiocarbamates, a dispersant or surface active agent may be included in the reaction mixture in an amount between 0.5 and 2 weight percent of the total weight of the reactants. Preferred dispersants and/or surface active agents include conventional anionic, cationic and nonionic agents.

EXAMPLE I

Dimethyldithiocarbamate is prepared by placing the following materials into a closed reaction chamber:

| Monomethylamine (40 percent) | 155.25 gms. |
|---|---|
| Carbon disulfide | 76.12 gms. |
| Water | 190.00 gms. |
| Dispersant (or surfactant) | 4.11 gms. |

The ingredients are stirred in a closed reactor for a period of time until it is observed that the pressure therein has fallen to below atmospheric pressure (about 5 hours). The reactor is then opened and the temperature raised to about 50° C. A 28.49 percent solution of dimethyldithiocarbamate is formed containing 15.07 weight percent sulfur. Water may be added to form solutions containing less than 28.72 percent by weight dimethyldithiocarbamate.

EXAMPLE II

Trimethyldithiocarbamate is prepared by placing the following materials into a closed reactor:

| Dimethylamine (40 percent) | 112.70 gms. |
|---|---|
| Monomethylamine (40 percent) | 77.62 gms. |
| Carbon disulfide | 76.12 gms. |
| Water | 204.40 gms. |

The above ingredients are added to a closed reactor with the reaction taking place in the same manner as set forth in Example I, above. One mole of trimethyldithiocarbamate as a 25.75 percent solution and containing 13.62 percent sulfur is produced.

Di- and trialkyldithiocarbamates are useful in combination with solvents and/or inert carriers whereby liquids, powders, emulsions, or finely divided solids are produced. Thus, according to a further embodiment of this invention, the novel, improved compounds of this invention are used in effective amounts with at least one inert carrier. Suitable inert carriers include water, alcohol, polyalcohols, acetone, and other organic solvents miscible with water.

EXAMPLE III

Dimethyldithiocarbamate is an excellent additive to pine oil disinfectants. A suitable concentrate comprises:

| Dimethyldithiocarbamate (see Example I) | 150 gms. |
|---|---|
| Pine Oil | 75.gms. |
| Potash soap | 8 gms. |
| Water | 7 gms. |

One part of this concentrate is diluted with 100 parts water and is useful as a general household and industrial spray.

EXAMPLE IV

In order to illustrate the outstanding fungicidal properties of the compounds of this invention when compared to the prior art, an alkyl ester of alkyldithiocarbamic acid was produced in accordance with the teachings of U.S. Pat. No. 2,127,375. The compounds produced therein are regarded as fungicides by U.S. Pat. No. 1,972,961. For purposes of comparison, the dodecyl ester of diethyldithiocarbamic acid was prepared in accordance with Example I, of U.S. Pat. No. 2,127,375.

For comparative purposes, the tests were conducted with the methyl ester of monomethyl dithiocarbamate which was prepared in accordance with the steps set forth in Example I, above. The compound of this invention was compared with the prior art compound noted above, for fungicidal activity with respect to *Rhizoctonia solani*, *Phytophthora cinnamoni* and *Fusarium oxysporium*. As a result of these tests, which were conducted under identical conditions, it was apparent that the compound of this invention (A) exhibited fungicidal properties at concentrations as low as 60 ppm for all three fungi whereas the prior art compound (B) requires 250 ppm to prevent growth of two of the test fungi. The results of these tests are set forth in the following Table:

TABLE

| Test Fungi Used | Concentration of toxicants in parts per million in the same suspension medium | | | | | | | | | | | | | |
| --- | --- | --- | --- | --- | --- | --- | --- | --- | --- | --- | --- | --- | --- | --- |
| | 1,000 | | 500 | | 250 | | 120 | | 60 | | 30 | | 0 | |
| | A | B | A | B | A | B | A | B | A | B | A | B | A | B |
| Rhizoctonia solani | − | − | − | − | − | − | − | − | − | + | + | + | + | + |
| Phytophthora cinnamomi | − | − | − | − | − | + | − | + | − | + | + | + | + | + |
| Fusarium oxysporium | − | − | − | − | − | + | − | + | − | + | + | + | + | + |

− = fungicidal, no growth of mycelium.
+ = not fungicidal, growth of mycelium.

What is claimed is:

1. A process for preparing a compound of the formula:

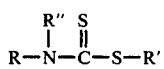

wherein R and R' are each alkyl groups containing from 1 to 6 carbon atoms and R" is hydrogen or an alkyl group containing from 1 to 6 carbon atoms, said compound being free of alkali metal, of side products from reactions resulting from the use of an alkali metal hydroxide in synthesis of said compound, and free of ethylene thiourea; and said compound being substantially free of color, water-soluble, and forming clear solutions with water;

said process comprising the steps of (a) reacting a first compound of the formula RR"NH wherein R is an alkyl group of 1 to 6 carbon atoms and R" is hydrogen or an alkyl group of 1 to 6 carbon atoms, a second compound of the formula R'NH$_2$ wherein R' is an alkyl group of 1 to 6 carbon atoms, and CS$_2$ is aqueous solution, said reaction being carried out in said aqueous solution within an enclosed chamber for a period of time sufficient to permit the pressure therein to fall below an atmospheric pressure of about 760 mm. Hg., whereby said compound and ammonia are formed, (b) opening the reactor and removing the ammonia, and (c) recovering said compound.

2. The process of claim 1, wherein R" in said first compound is an alkyl group of 1 to 6 carbon atoms.

3. The process of claim 1, wherein R" in said first compound is hydrogen.

4. The process of claim 1 wherein R, R' and R" are each methyl.

* * * * *